United States Patent [19]

Kawamura et al.

[11] Patent Number: 4,889,943

[45] Date of Patent: Dec. 26, 1989

[54] METHOD FOR STABILIZING AQUEOUS PHOSPHOENOLPYRUVIC ACID SOLUTION

[75] Inventors: Hirotaka Kawamura; Norio Ohtsu, both of Ube; Shinichiro Utiumi, Tokyo, all of Japan

[73] Assignee: Ube Industries, Ltd., Ube, Japan

[21] Appl. No.: 126,602

[22] Filed: Nov. 30, 1987

[30] Foreign Application Priority Data

Dec. 5, 1986 [JP] Japan .................................. 61-288937
Dec. 12, 1986 [JP] Japan .................................. 61-294750

[51] Int. Cl.$^4$ .......................... C07C 9/09; A61B 19/00
[52] U.S. Cl. ........................................ 558/71; 604/410
[58] Field of Search ............................................ 558/71

Primary Examiner—Anton H. Sutto
Attorney, Agent, or Firm—Frishauf, Holtz, Goodman & Woodward

[57] ABSTRACT

Disclosed is a method for stabilizing an aqueous solution of phosphoenolpyruvic acid and its salt, which comprises placing the solution under the condition of pH 10 to 13.

Disclosed is also a container for phosphoenolpyruvic acid, comprising an outer bag comprising a polyvinyl chloride type resin and an inner bag comprising an alkali resistant resin for storing an aqueous solution of phosphoenolpyruvic acid or its salt under the condition of pH 10 to 13 therein.

According to the present invention, a method for stabilizing phosphoenolpyruvic acid in an aqueous solution and a container for housing the stabilized phosphoenolpyruvic acid accompanied therewith can be obtained.

12 Claims, 1 Drawing Sheet

METHOD FOR STABILIZING AQUEOUS PHOSPHOENOLPYRUVIC ACID SOLUTION

BACKGROUND OF THE INVENTION

This invention relates to a method for stabilizing an aqueous phosphoenolpyruvic acid solution and a container therefor. Phosphoenolpyruvic acid (hereinafter called "PEP") is a compound represented by the following formula:

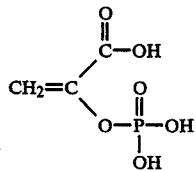

and it is generally expected to be used in the form of sodium salt as the blood preservative and the medicament for activation (Journal of Transfusion Society of Japan, 32, 310 (1986); Japanese patent application No. 127320/1986).

However, PEP is unstable in an aqueous solution and susceptible to hydrolysis. Particularly, as the treatment temperature is higher, this tendency becomes marked during high pressure sterilization in an autoclave.

Therefore, it has been desired to develop a means for stabilizing PEP in an aqueous solution and a container for housing the stabilized PEP accompanied therewith.

SUMMARY OF THE INVENTION

PEP is ordinarily used together with citric acid, sodium citrate, sodium dihydrogen phosphate, maltose, adenine, etc. but it is unstable under neutral acidic conditions. As the result of investigations by the present inventors, it has been clarified that stable storage of PEP can be accomplished by placing an aqueous solution of PEP or its salt under the condition of pH 10 to 13.

Also, the present inventors have found that a container, comprising an outer bag comprising a polyvinyl chloride type resin and an inner bag comprising an alkali resistant resin for storing an aqueous solution of phosphoenolpyruvic acid or its salt under the condition of pH 10 to 13 therein can specifically accomplish stable storage of PEP.

DESCRIPTION OF THE PREFERRED EMBODIMENTS

The salt of PEP to be used in the present invention may include, for example, sodium salt, potassium salt, lithium salt, etc.

According to the present invention, an aqueous solution of PEP or its salt is placed under the condition of pH 10 to 13, preferably under the condition of pH 10 to 12, and particularly preferably under the condition of pH 11 to 12.

The concentration of the aqueous solution of PEP or its salt is not particularly limited provided that it is not more than the saturated concentration. As the base to be used for adjusting the pH of the above aqueous solution, for example, sodium hydroxide, potassium hydroxide, lithium hydroxide, etc. may be employed.

The aqueous solution of PEP or its salt stabilized according to the method of the present invention can be adjusted to an appropriate pH during usage and used for various uses.

Next, the container for PEP is to be described. In the prior art, as the blood bag, those made of polyvinyl chloride type resins have been used for good workability by fusion, flexibility and good storability of blood cells.

However, polyvinyl type resins conventionally used for blood bag will be denatured when contacted with a solution of pH 10 or higher. As the container for PEP which is able to embody the above PEP stabilizing method, a structure making a polyolefin having alkali resistance connected to a blood bag may be conceivable, but due to extremely poor fusion of a polyolefin with polyvinyl chloride, a bag of a polyolefin cannot be connected to a blood bag made of polyvinyl chloride.

Therefore, as the means capable of embodying the above storing method, a novel container for PEP being easy in workability and capable of housing an alkaline solution is required.

In the present invention, as the polyvinyl chloride type resin, there may be included polyvinyl chloride, polyvinylidene chloride and copolymers comprising vinyl chloride or vinylidene chloride as the main starting material.

As the alkali resistant resin, there may be included, for example, polyolefins such as polyethylene, polypropylene, etc. and copolymers comprising an olefin such as ethylene, propylene, etc. as the main starting material.

Figure 1:
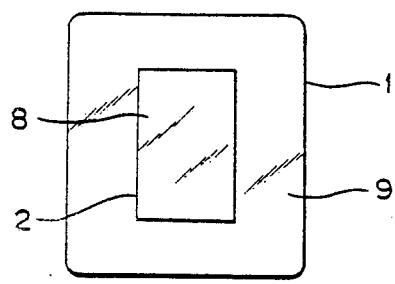
FIG. 1 is a schematic illustration of the container for PEP of the present invention.

FIG. 1 shows schematically the medicament container of the present invention.

In the present invention, the inner bag 2 may be either not fixed to the outer bag 1 or fixed by an appropriate means. Also, in the figures, 3 shows a parent bag, 4, 5 and 6 child bags, 7 a sampling needle, 8 an alkaline solution and 9 a neutral or acidic solution, respectively.

The medicament container of the present invention is required to have a structure such that the content of the inner bag 2 may be released during usage and the alkaline solution housed therein may be mixed with the neutral or acidic solution housed in the outer bag 1. That is, during storage of the container, it is required that the solutions in the inner bag 2 and the outer bag 1 should not contact each other.

As the means for providing such a structure, for example, there may be included manufacturing of an inner bag 2 with a thickness which is made extremely thinner than that of the outer bag 1 so that the inner bag 2 may be punctured by pressing of the container by means of a pointed head provided innerside of the outer bag 1; manufacturing of an inner bag 2 having an edge with a cutting so that it can be readily torn off from outside of the outer bag 1; manufacturing of an inner bag 2 having a structure such that a stopper is provided on the inner bag 2 and the stopper of the inner bag 2 can be readily plucked out by bending of the outer bag 1.

Figure 2:
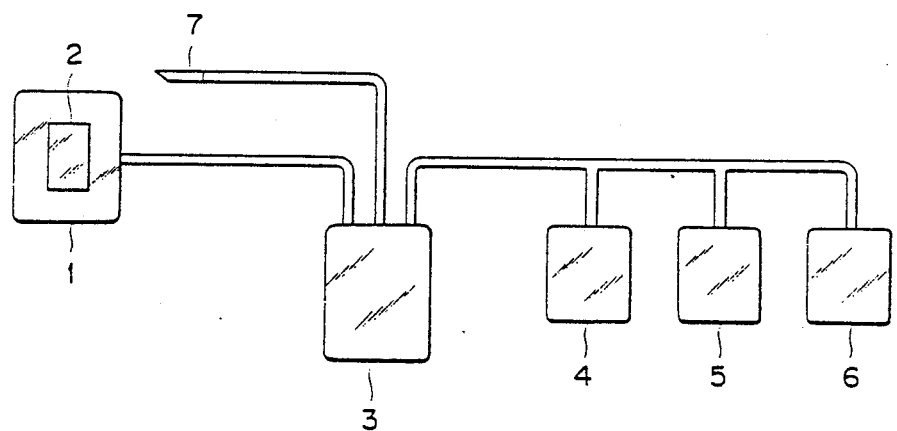
FIG. 2 is an illustration showing one example of the blood bag system for attachment of the container for PEP of the present invention thereto.

Referring now to FIG. 2, the medicament container of the present invention is described when used for a blood bag.

In the inner bag 2, an aqueous solution of PEP or its salt (hereinafter called "first solution") is housed with its pH being adjusted to 10 to 13, preferably 10 to 12, particularly preferably 11 to 12 as mentioned above. As the salt of PEP, for example, sodium salt, potassium salt, lithium salt, etc. may be included. As the base to be used for adjusting the pH of the above aqueous solution to 10 to 13, for example, sodium hydroxide, potassium hydroxide, lithium hydroxide, etc. may be included. The concentration of the aqueous solution of PEP or its salt is not particularly limited, provided that it is not higher than the saturated concentration.

In the outer bag 1, an aqueous solution of the components other than PEP and its salt (hereinafter called "second solution") is housed. Such components may include, for example, disaccharides such as maltose, sucrose; monosaccharides such as galactose, mannitol; citric acid, sodium citrate, sodium dihydrogen phosphate and adenine, etc., but a compound other than the above compounds which is suitable for storage of blood and will not denature the outer bag comprising polyvinyl chloride type resin may be also used.

The first solution and the second solution should preferably be adjusted previously to the respective pH's and volumes so that the pH when both solutions are mixed may become 5.5 to 7.5.

After the container for PEP manufactured as described above is subjected to high sterilization, the inner bag 2 is opened, the solution obtained by mixing of the first solution and the second solution is led to a parent bag 3, wherein said solution is mixed with an erythrocyte concentrate or erythrocytes obtained by removal of plasma, leucocytes and platelets from an erythrocyte concentrate and the parent bag 3 housing the mixed suspension is stored at 4° C., whereby erythrocytes which have an excellent function can be stored stably for a long term.

The use of the container for PEP is not limited to blood bag, but can be used widely for housing an alkaline solution and a neutral or acidic solution as separated from each other.

The present invention is described in more detail by referring to Examples, but these Examples do not limit the scope of the present invention at all.

EXAMPLE 1

An aqueous 2% PEP solution of which pH was adjusted with 1 N NaOH was stored at room temperature for 60 days and its stability was examined.

In the solution with pH=7.4, PEP was gradually decomposed. The decomposition rate were 0.8% and 1.4% after 28 days and 60 days, respectively. In the solution with pH=12, PEP was found to be stable without any decomposition observed after 60 days.

EXAMPLE 2

For confirmation of thermal stability depending on the liquid property of PEP, the following experiments were conducted. An aqueous 2% PEP solution was prepared, adjusted in pH with 1N aqueous sodium hydroxide and autoclaved (121° C., 30 min.), followed by measurement of decomposition percentage. The results are shown in Table 1.

TABLE 1

| pH | 7 | 8 | 9 | 10 | 10.5 | 11 | 11.5 | 12 |
|---|---|---|---|---|---|---|---|---|
| Decomposition | 79.7 | 28.9 | 24.0 | 17.9 | 13.2 | 7.3 | 4.6 | 1.0 |

TABLE 1-continued

| pH | 7 | 8 | 9 | 10 | 10.5 | 11 | 11.5 | 12 |
|---|---|---|---|---|---|---|---|---|
| percentage | | | | | | | | |

As the liquid property is migrated to alkaline region, stability is increased until substantially no decomposition of PEP was observed at pH=12.

EXAMPLE 3

A container housing the first solution and the second solution respectively in the inner bag made of polypropylene and outer bag made of polyvinyl chloride was prepared.

| First solution | PEP | 1.57 g |
|---|---|---|
| | (dissolved in distilled water for injection, adjusted to pH = 12 with 1N NaOH and then the total volume was made up to 20 ml) | |
| Second solution | Maltose | 9.2 g |
| | Sodium citrate | 2.0 g |
| | Citric acid | 1.4 g |
| | Sodium dihydrogen phosphate | 0.14 g |
| | Adenine | 0.01 g |
| | (dissolved in distilled water for injection and the total volume made up to 130 ml) | |

The container was subjected to high pressure sterilization in an autoclave at 121° C. for 20 minutes. The PEP amount after the sterilization was the same as before. After the sterilization, the inner bag was punctured. The pH after mixing of the first solution and the second solution was about 6.5. Fresh human erythrocyte concentrate in a parent bag was centrifuged, and the above mixture was added to 150 ml of the human erythrocyte concentrate obtained by removal of the plasma and the buffy coat layer (the erythrocyte had a hematocrit value of 95%) to prepare an erythrocyte suspension. At this time, said suspension had a hematocrit value of about 45%).

The erythrocyte suspension as prepared above was stored together with the container at 4° C. for 6 weeks. The erythrocyte suspension was sampled every one week for measurement of the contents of 2,3-diphosphoglyceric acid (hereinafter called "2,3-DPG") and adenosine triphosphate (hereinafter called "ATP") in erythrocyte. Measurement was performed after incubation for one hour after sampling. Also, the extent of hemolysis was similarly examined. The erythrocyte concentrate by use of the currently practiced CPD solution was served as the control group. The results are shown in Table 2 and Table 3. Table 2 shows an amount of 2,3-DPG and ATP as a function of time by week. Table 3 shows a degree of hemolysis as a function of time by week.

TABLE 2

| | Week | 0 | 1 | 2 | 3 | 4 | 5 | 6 |
|---|---|---|---|---|---|---|---|---|
| Applied example of this invention (μM/gHb) | 2,3-DPG | 45 | 35 | 23 | 14 | 12 | 8 | 6 |
| | ATP | 6.2 | 6.8 | 6.3 | 6.0 | 5.7 | 4.9 | 4.2 |
| Control (μM/gHb) | 2,3-DPG | 13 | 12 | 6 | 2 | — | — | — |
| | ATP | 4.0 | 3.8 | 3.5 | 3.1 | — | — | — |

TABLE 3

| Week | 0 | 1 | 2 | 3 | 4 | 5 | 6 |
|---|---|---|---|---|---|---|---|
| Applied example of this invention (μM/gHb) | 12 | 21 | 22 | 28 | 37 | 50 | 59 |
| Control (μM/gHb) | 14 | 30 | 65 | 105 | — | — | — |

According to the storage method of the present invention, PEP and its salt can be stored stably.

The container for PEP of the present invention has easiness of workability and also can house an alkaline solution and a neutral or acidic solution as separated from each other.

We claim:

1. A method for stabilizing an aqueous solution of phosphoenolpyruvic acid or its sodium salt, which comprises admixing NaOH with said aqueous solution in an amount such that the pH of the resultant solution is from 10 to 13.

2. The method according to claim 1, wherein said pH is 10 to 12.

3. The method according to claim 1, wherein said pH is 11 to 12.

4. The method according to claim 1, wherein an aqueous solution of NaOH is admixed with said aqueous solution of phosphoenolpyruvic acid or its sodium salt.

5. The method according to claim 2, wherein an aqueous solution of NaOH is admixed with said aqueous solution of phosphoenolpyruvic acid or its sodium salt.

6. The method according to claim 3, wherein an aqueous solution of NaOH is admixed with said aqueous solution of phosphoenolpyruvic acid or its sodium salt.

7. The method according to claim 1, wherein an aqueous solution of NaOH is admixed with said aqueous solution of phosphoenolpyruvic acid.

8. The method according to claim 2, wherein an aqueous solution of NaOH is admixed with said aqueous solution of phosphoenolpyruvic acid.

9. The method according to claim 3, wherein an aqueous solution of NaOH is admixed with said aqueous solution of phosphoenolpyruvic acid.

10. The method according to claim 1, wherein an aqueous solution of NaOH is admixed with said aqueous solution of a sodium salt of phosphoenolpyruvic acid.

11. The method according to claim 2, wherein an aqueous solution of NaOH is admixed with said aqueous solution of a sodium salt of phosphoenolpyruvic acid.

12. The method according to claim 3, wherein an aqueous solution of NaOH is admixed with said aqueous solution of a sodium salt of phosphoenolpyruvic acid.

* * * * *